(12) United States Patent
Shindledecker et al.

(10) Patent No.: US 10,836,988 B2
(45) Date of Patent: Nov. 17, 2020

(54) LABORATORY INSTRUMENT INDUSTRIAL DESIGN CUSTOMIZATION FOR CUSTOMER PERSONALIZATION

(71) Applicant: BECTON, DICKINSON AND COMPANY, Franklin Lakes, NJ (US)

(72) Inventors: Scott Shindledecker, Jarrettsville, MD (US); Edward Skevington, Stewartstown, PA (US); Brent Ronald Pohl, Timonium, MD (US); Dustin Diemert, Baltimore, MD (US); Thierry Guillet, Baltimore, MD (US)

(73) Assignee: BECTON DICKINSON AND COMPANY, Franklin Lakes, NJ (US)

( * ) Notice: Subject to any disclaimer, the term of this patent is extended or adjusted under 35 U.S.C. 154(b) by 258 days.

(21) Appl. No.: 15/574,196

(22) PCT Filed: May 27, 2016

(86) PCT No.: PCT/US2016/034584
§ 371 (c)(1),
(2) Date: Nov. 15, 2017

(87) PCT Pub. No.: WO2016/191657
PCT Pub. Date: Dec. 1, 2016

(65) Prior Publication Data
US 2018/0133709 A1 May 17, 2018

Related U.S. Application Data

(60) Provisional application No. 62/167,429, filed on May 28, 2015.

(51) Int. Cl.
*C12M 3/00* (2006.01)
*C12Q 1/18* (2006.01)
(Continued)

(52) U.S. Cl.
CPC .............. *C12M 23/46* (2013.01); *B01L 3/54* (2013.01); *C12Q 1/18* (2013.01); *G01N 33/483* (2013.01);
(Continued)

(58) Field of Classification Search
CPC .... B01L 1/00; B01L 3/54; B01L 99/00; B01L 2200/02; B01L 2200/087; C12M 23/46;
(Continued)

(56) References Cited

U.S. PATENT DOCUMENTS 4,732,431 A * 3/1988 Mason .................. E06B 5/006
312/109
4,923,816 A 5/1990 Heeg
(Continued)

FOREIGN PATENT DOCUMENTS

| CN | 1257353 A | 6/2000 |
|---|---|---|
| CN | 103221897 A | 7/2013 |

(Continued)

OTHER PUBLICATIONS

Chinese Office Action and Search Report issued in CN application No. 201680030083.6 dated Jul. 25, 2019.
(Continued)

*Primary Examiner* — William H. Beisner
*Assistant Examiner* — Danielle B Henkel
(74) *Attorney, Agent, or Firm* — Botos Churchill IP Law LLP (57) ABSTRACT

A customizable laboratory instrument comprising an interior space for receipt of test materials therein. An indented exterior surface of the laboratory instrument defines a boundary surface, a backing surface, and a sidewall. The backing surface is offset from the boundary surface a distance substantially equal to a depth of the sidewall. A panel having an edge is attachable to the sidewall such that a space
(Continued)

is formed between the panel and backing surface for receipt of an object therein.

21 Claims, 7 Drawing Sheets

(51) Int. Cl.
    *G01N 33/483* (2006.01)
    *G09F 23/00* (2006.01)
    *G09F 3/20* (2006.01)
    *B01L 3/00* (2006.01)
    *B01L 99/00* (2010.01)

(52) U.S. Cl.
    CPC ............... *G09F 3/20* (2013.01); *G09F 23/00* (2013.01); *B01L 99/00* (2013.01); *B01L 2200/02* (2013.01); *B01L 2200/087* (2013.01)

(58) Field of Classification Search
    CPC .......... C12Q 1/18; G01N 33/483; G09F 3/20; G09F 23/00
    See application file for complete search history.

(56) References Cited

U.S. PATENT DOCUMENTS

| | | | |
|---|---|---|---|
| 6,461,287 B1 | 10/2002 | Glater | |
| 6,948,272 B1* | 9/2005 | Olivier | G09F 7/18 40/331 |
| 7,014,281 B2* | 3/2006 | Wuestefeld | A47L 15/4265 126/194 |
| 8,622,487 B2* | 1/2014 | Jung | D06F 39/12 312/204 |
| 8,763,802 B2 | 7/2014 | Ellis-Brown | |
| 2001/0035445 A1 | 11/2001 | Kameya | |
| 2003/0085230 A1 | 5/2003 | Hessler | |
| 2004/0068907 A1* | 4/2004 | Bazany | B65D 25/205 40/642.02 |
| 2005/0009195 A1 | 1/2005 | Wang | |
| 2005/0084956 A1 | 4/2005 | Tamaoki | |
| 2008/0153078 A1 | 6/2008 | Braman | |
| 2008/0203870 A1* | 8/2008 | Riley | A47J 31/44 312/265.6 |
| 2011/0000115 A1 | 1/2011 | Ashby | |
| 2015/0050725 A1 | 2/2015 | Pieczarek | |
| 2018/0133709 A1 | 5/2018 | Shindledecker et al. | |

FOREIGN PATENT DOCUMENTS

| | | |
|---|---|---|
| CN | 206463980 U | 9/2017 |
| JP | 2009036821 A | 2/2009 |
| RU | 2651279 C1 | 4/2018 |
| WO | 2015042583 A2 | 3/2015 |

OTHER PUBLICATIONS

EP Communication issued in corresponding EP application No. 16800783, dated Dec. 4, 2016.
International Search Report from PCT Application No. PCT/US2016/034584 dated Oct. 12, 2016.
EP Communication issued in corresponding EP application No. 16800783.9 dated Nov. 11, 2019.
British Telecom: "BT Vanguard User Manual", Jan. 1, 1992, XP055639067, Retrieved from Internet: URL: http://www.telephonesuk.co.uk/user_guides/Corded_phones/Vanguard.pdf [retrieved on Nov. 5, 2019], pp. 6.
Japanese Office Action for Application No. 2017-571972 dated Apr. 4, 2020, pp. 6.
Decision to Grant from Russian Application No. 2017145142 dated Apr. 2, 2020.
EP Communication issued in corresponding EP application No. 16800783.9 dated Jun. 18, 2020.

\* cited by examiner

LABORATORY INSTRUMENT INDUSTRIAL DESIGN CUSTOMIZATION FOR CUSTOMER PERSONALIZATION

CROSS-REFERENCE TO RELATED APPLICATION

The present application is a national phase entry under 35 U.S.C. § 371 of International Application No. PCT/US2016/034584 filed May 27, 2016 published in English, which claims priority from U.S. Provisional Application No. 62/167,429 filed May 28, 2015, all of which are incorporated herein by reference.

BACKGROUND OF THE INVENTION

Modern laboratories, including microbiology laboratories and the like, include numerous instruments placed throughout its floor space and in the line of sight of its occupants. Such instruments can be bulky and sit on table tops or as stand-alone units and are often positioned in front of walls where artwork might normally be located. Laboratories typically have strict requirements for sanitation and occupants of such laboratories desire instruments that are easily sanitized. However, laboratory instruments designed to perform specific functions and allow for ease of sanitation often comes at the expense of aesthetic qualities and customizable appearance. Thus, in addition to potentially interfering with the placement of artwork or other aesthetic features, current instruments lack of aesthetic qualities and/or customizable appearance can make individual instruments intimidating and the overall laboratory environment dreary. Such dreariness can impact the mood and productivity of the laboratory's occupants.

BRIEF SUMMARY OF THE INVENTION

The present disclosure describes exemplary devices and methods that allow for laboratory instruments to be personalized and customized in appearance, without any detriment or degradation of functionality, thereby providing aesthetic appeal to the laboratory environment. The features that allow for customizable appearance do not make it more difficult to clean or operate the instruments, thereby preserving a clean laboratory environment in which the instruments operate normally In one aspect of the present disclosure, a customizable laboratory instrument includes a housing defining an interior space for receipt of test materials therein. The housing includes at least one exterior surface that has an indented backing surface with a raised boundary surface at at least a portion of its perimeter, and a sidewall. The backing surface is offset from the boundary surface a distance substantially equal to a depth of the sidewall. The customizable laboratory instrument also includes a panel having an edge adapted to be received by the sidewall such that a space is defined between the panel and backing surface for receipt of a decorative object therein.

Additionally, the instrument may be an ID/AST instrument. The exterior surface may be located on a door of the instrument or on an exposed surface of the instrument. The sidewall may slope outwardly from the boundary surface to the backing surface forming a channel therebetween for receipt of the panel.

Continuing with this aspect, the panel may include a plurality tabs extending from an edge thereof and the sidewall may include a plurality of slots extending therein, wherein each slot may be adapted to receive a respective panel tab. The tabs on one side of the panel may be longer than the tabs on the opposite side of the panel. At least one of the tabs may extend from the edge a longer distance than the remainder of the tabs. Also, the slots may be arranged to cause the panel to curve when the panel tabs are disposed in the slots.

Furthermore, the sidewalls may define a quadrilateral and at least one of the sidewalls that define the quadrilateral may include at least one slot. The panel may also be a quadrilateral complementary to that defined by the sidewalls, and at least two or more sides of the panel edge may each include at least one tab to be received by a corresponding slot in the sidewall. A first panel edge may have at least four tabs, and a second panel edge may include at least four tabs. A first and second tab of the first panel edge may extend along the first panel edge a longer distance than a third and fourth tab of the first panel edge.

In another aspect of the present disclosure, a customizable laboratory instrument includes a housing defining an interior space for receipt of test materials therein. The instrument also includes a door for access to the interior space. The door has an exterior surface comprising a raised boundary surface surrounding a recessed backing surface, and a sidewall. The recessed backing surface is offset from the boundary surface a distance substantially equal to a depth of the sidewall. Also included in the instrument is a panel having at least one edge adapted to be received by the sidewall wherein an object can be removably placed between the panel and backing surface.

Additionally, the instrument may be an ID/AST instrument. The panel may also include a plurality tabs extending from an edge thereof and the sidewall may include a plurality of slots extending therein for receipt of the tabs. The sidewall may define a quadrilateral such that two opposite sidewalls each include a plurality of slots. The tabs on one edge of the panel may extend further from that edge than the tabs on the opposite edge of the panel.

BRIEF DESCRIPTION OF THE DRAWINGS

The features, aspects, and advantages of the present invention will become better understood with regard to the following description, appended claims, and accompanying drawings in which:

DETAILED DESCRIPTION

As used herein, the terms "about," "generally," and "substantially" are intended to mean that slight deviations from absolute are included within the scope of the term so modified.

Figure 1:
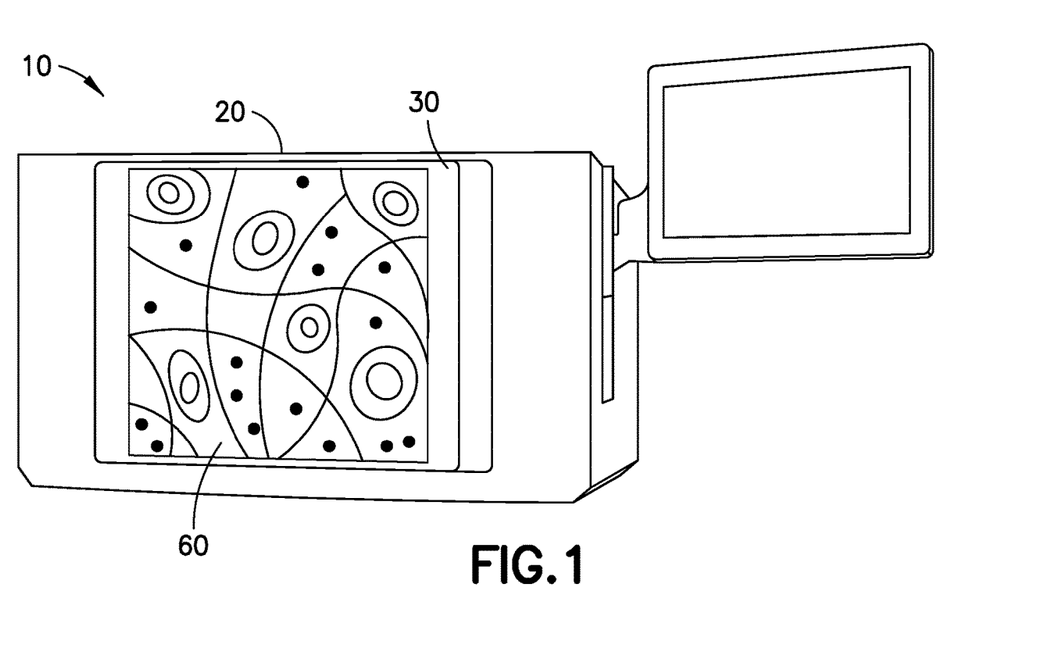
FIG. 1 is a perspective view of an exemplary laboratory instrument that includes a customizable door for aesthetic appeal.

FIG. 1 depicts an exemplary laboratory instrument 10 in the form of an identification and antibiotic susceptibility (ID/AST) instrument. Such instrument 10 includes a housing 20 or body for receiving test materials and a door 30 for enclosing such materials therein. Door 30 includes a front panel 60 that assists in the display of artwork or other materials of the laboratory occupants' choosing, which may be of an aesthetic quality.

While the present disclosure discusses instrument personalization in the context of the exemplary ID/AST instrument throughout, it should be understood that this is merely an example of one of the many instruments to which the principles disclosed herein can be applied.

FIGS. 2-7B depict door 30, which is customizable to carry aesthetic/decorative features, such as paintings, drawings, and the like or other objects, such as instructions for using instrument 10. Door 30 includes a front side 40 and a rear or interior side 50. Rear side 50 (best shown in FIGS. 3 and 4) includes a projecting portion 52, which when closed, projects into a cavity within housing 20. The depth of door 30 is generally the greatest at projecting portion 52 which may be helpful for thermally insulating an environment within housing 20. Other than the depth of door 30, the insulative properties of projecting portion 52 can be further adjusted by the inclusion of insulating material within a space within projecting portion 52. Such insulation can include air, solid insulation or foam insulation, for example. In addition, projecting portion 52 can taper inwardly from all sides thereof to correspond with a complementary taper formed by housing 20 in order to provide a tight seal, which can be a hermetic seal or a light tight and air resistant seal, when door 30 is closed.

Figures 2, 3:
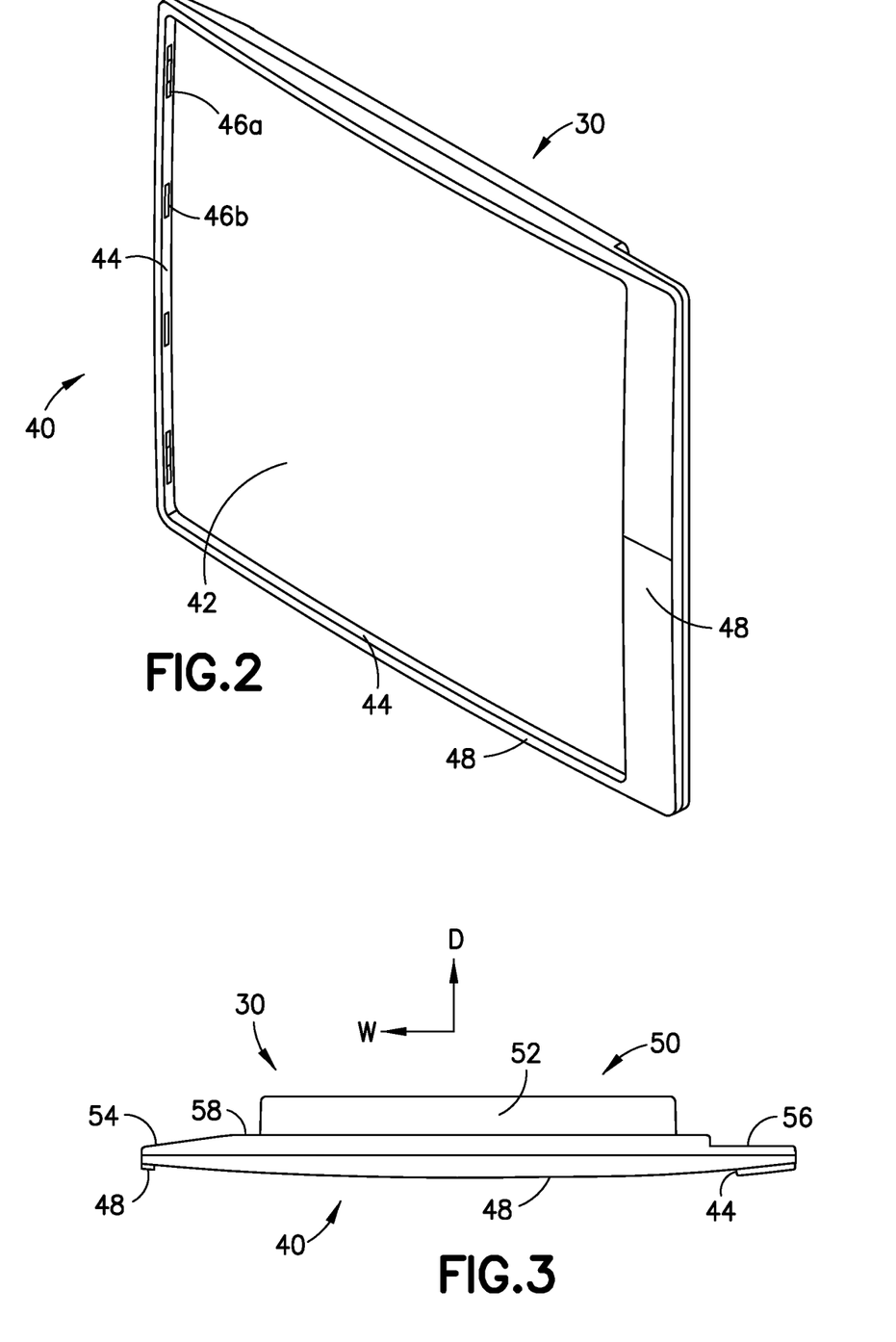
FIG. 2 is a perspective view of the door of FIG. 1.
FIG. 3 is a top view of the door of FIG. 1 with corresponding width and depth directions.
Figure 4:
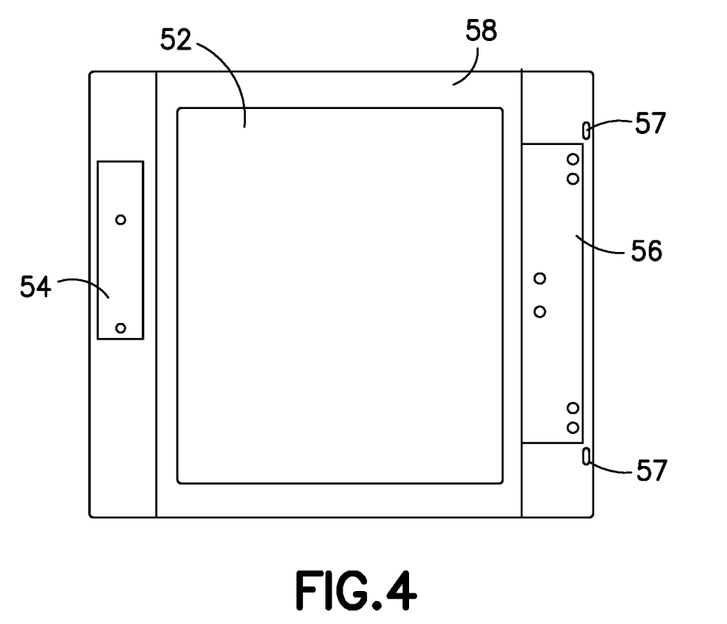
FIG. 4 is rear view of the door of FIG. 1.
Figure 5:
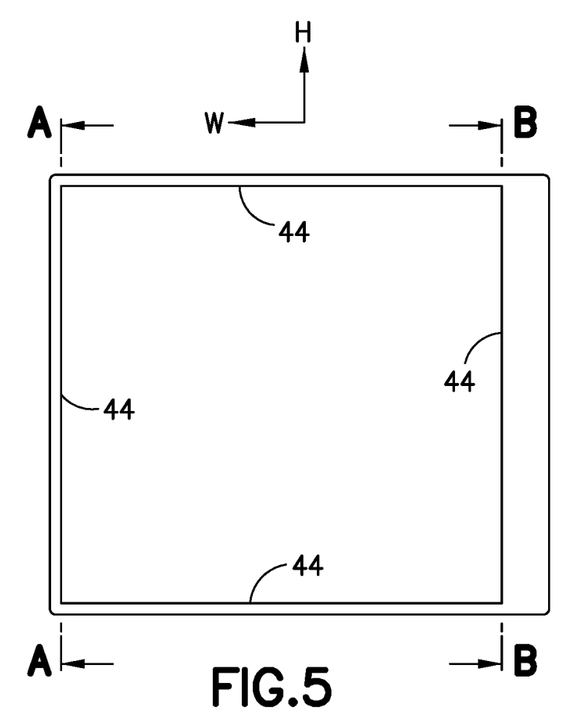
FIG. 5 is a front view of the door of FIG. 1 with corresponding height and width directions.
Figure 6:
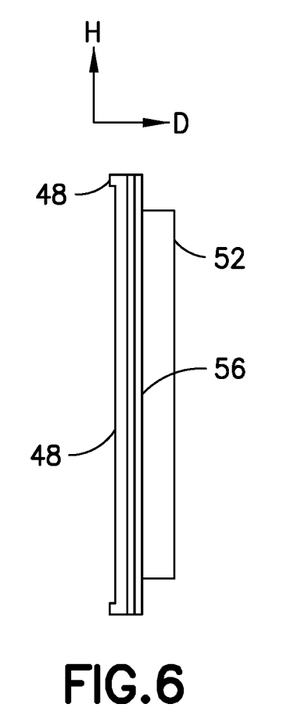
FIG. 6 is a side view of the door of FIG. 1 with corresponding height and depth directions.

A planar abutment surface 50 surrounds projecting portion 52, which may be complementary to and abut a surface on housing 20 to further provide sealing engagement with the housing. A hinge side of door 30 includes a sloping surface 56 that extends away from abutment surface 58. Sloping surface 56 may provide clearance space for the door as it is closed. A latch side of door 30 includes an offset surface 54 that is offset from abutment surface 58.

Other rear side configurations are contemplated to suit the particular function of the instrument. For example, in one embodiment, rear side 50 can be completely flat or concave and may have other engagement features not described herein. Additionally, door 30 can be configured to slide linearly for opening and closing and, therefore, be devoid of a hinge. In addition, a latch or locking mechanism may be located at an edge intermediate the front side and rear side. Regardless of the configuration of rear side 50, the below discussion regarding front side 40 is equally applicable.

Front side 40 or exterior side (best shown in FIGS. 2 and 5-7B) of door 30 has an exterior surface that is indented or recessed to form a backing surface 42, boundary surface 48, and sidewall 44. Boundary surface 48 defines a front side extent of door 30 (although other objects may extend beyond the boundary surface) and surrounds backing surface 42.

Backing surface 42 is offset from boundary surface 48, which may be a distance equal to a depth of sidewall 44.

Backing surface 42, as depicted, is in the shape of a quadrilateral, although other shapes, such as a circle or oval, are contemplated. Backing surface 42, as depicted, is a flat, planar surface. However, backing surface 42 can be curved as described further below.

Sidewall 44 is preferably planar and spans between boundary surface 48 and backing surface 42. Sidewall 44 generally defines the perimeter of backing surface 42. Thus, as shown, when backing surface 42 is a quadrilateral, sidewall 44 extends along the four-sided perimeter. Sidewall 44 includes a plurality of slots 46a-h (best shown in FIGS. 2, 7A, & 7B) disposed in at least two of the sidewall's sides, which are preferably disposed opposite each other. However, in some embodiments, slots 46a-h can be disposed in one or more of the sides of sidewall 44. Each slot 46a-h is dimensioned to receive a tab of a panel, as is described in more detail further below.

Rear side 50 of door 30 includes openings 57 (best shown in FIG. 4) that extend into door 30 and communicate with slots 46a-d, and more particularly slots 46a and 46d. Such openings 57 extend into door 30 from a hinge side of the door 30 for ease of access when door 30 is open. However, such openings 57 can be included on a latch side of door 30 for access to slots 46e-h. Openings 57 are configured to receive an elongate tool to assist in removing a panel from door 30.

Figure 8A:
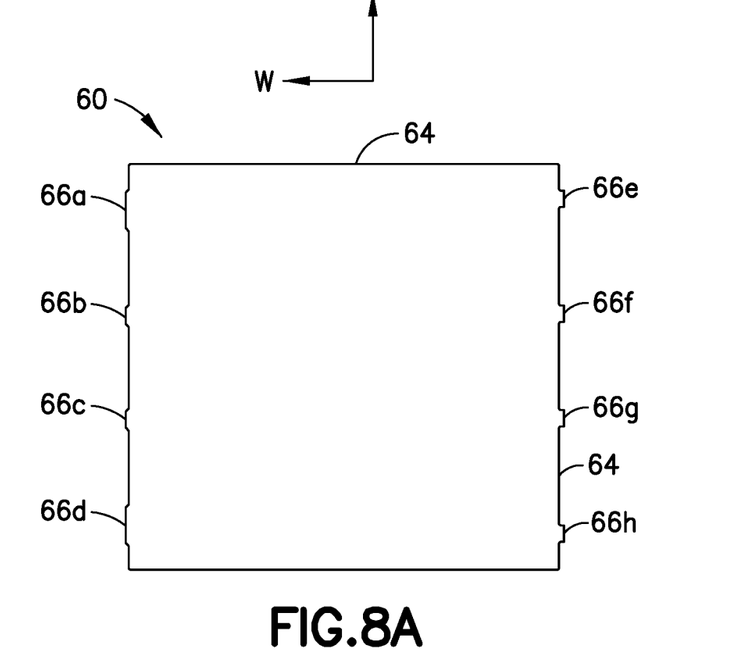
FIG. 8A is a front view of a panel.
Figure 8B:
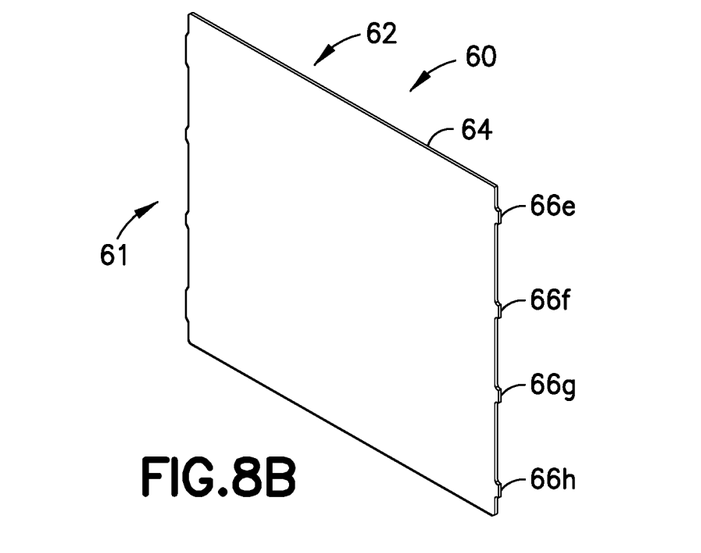
FIG. 8B is a perspective view of the panel.

FIGS. 8A and 8B depict an exemplary panel 60, which is attachable to sidewall 44 of door 30. Panel 60 is preferably made from material that is sufficiently clear/transparent to complement a user's design choice and to complement a theme and/or decorative feature. For example, panel 60 may be optically clear or may have a tint, such as, for example, a smoky blue tint to complement a color theme within the laboratory and/or to accentuate certain aspects of a decorative feature placed behind panel 60. In addition, panel 60 may be flexible and made from a material that can withstand repeated exposure to laboratory cleaning agents, such as bleach and the like. Exemplary materials from which panel can be made include acrylic, polycarbonate (PC), polymethyl methacrylate (PMMA), polyethylene terephthalate glycol (PET-G), polyethylene terephthalate (PET), high impact polystyrene (HIPS), styrene methyl methacrylate copolymer (SMMA), and flexible glass compositions.

Panel 60 has a front surface 61 and rear surface 62 each terminating at an edge 64. Edge 64 defines a perimeter thereof and a plurality of sides each corresponding with a side of sidewall 44 (FIG. 2). Edge 64 also defines a thickness/depth of panel 60. Panel 60 is preferably flexible and has a depth of about ⅛ of an inch (about 3.175 mm or about 125 mils) or less, which provides panel 60 with sufficient flexibility and resiliency. However, it should be understood that the depth of panel 60 may vary depending on the material selected. For example, the depth of panel 60 may be ⅛ of an inch or less where panel 60 is made from polycarbonate, but may be thicker when made from another material.

Panel 60 also includes a plurality of tabs 66a-h extending from edge 64. Each of tabs 66a-h is positioned along edge 64 so that when panel 60 is placed over backing surface 42 and within the frame formed by sidewall 44, tabs 66a-h can engage a corresponding slot 46a-h. Thus, in the depicted embodiment, two opposing sides of panel 60 each have tabs 66a-h extending from edge 64 at intervals along their respective lengths. In other embodiments, tabs 66a-h may be located on one or more sides of panel 60.

Additionally, tabs 66a-h may each extend an equal distance from edge 64 and extend an equal distance along edge

64. However, in other embodiments, some of tabs 66*e-h* may extend further from edge 64 and/or further along edge 64 than other tabs. For example, as depicted in FIG. 8A, tabs 66*e-h* extend further from the edge than tabs 66*a-d*. Additionally, tabs 66*a* and 66*d* extend along the edge a longer distance than tabs 66*b* and 66*c*. Slots 46*a-d* are dimensioned accordingly. This makes the panel easier to insert as the longer tabs are inserted first holding the panel in place as the shorter tabs are then snapped into their respective slots. The longer tabs also are better to secure the panel into the sidewall 44.

In the illustrated embodiment, when assembled, panel 60 is retained within the confines of sidewall 44 by tab and slot engagement. In addition, slots 46*a-h* may be offset from backing surface 42 a distance to form a space between panel 60 and backing surface 42 when panel 60 is engaged with sidewall 44. This space allows an aesthetic feature, such as a picture, drawing, painting or the like, which can be laminated, to be placed between panel 60 and backing surface 42 and retained in the space formed therebetween by panel 60.

In a method of use, instrument 10 may be provided with panel 60, which may be clear or transparent, and can be provided with one or more decorative features for placement between panel 60 and backing surface 42. However, instrument 10 can be provided with a colored panel, which is the same as panel 60 with the exception that one of its sides is painted or the material it is made from is tinted, as a placeholder until a decorative feature and panel 60 is selected at a later time.

Once the decorative feature is selected by a laboratory occupant or another end user, the decoration is placed on backing surface 42 and transparent panel 60 is placed over the decoration such that tabs 66*a-h* of panel 60 engage slots 46*a-h*. Thus, the decorative feature is retained in a space between panel 60 and backing surface 42. Aside from holding the decoration in place, panel 60 also acts as a barrier to the environment to help keep the space and decoration clean. In addition, panel 60 can be wiped down or otherwise sanitized along with the remainder of instrument 10 without significant alterations to the laboratory's cleaning routine. As desired, panel 60 can be easily removed by disengaging tabs 46*a-h* from slots 66*a-h* so that the decoration behind panel 60 may also be sanitized or replaced when desired to help maintain a fresh environment and maintain a contemporary feel.

While instrument personalization is discussed above in the exemplary context of door 30, it should be understood that other surfaces of the instrument exposed to the laboratory environment can be customized as described herein. For example, a side or top surface of housing 20 can be indented/recessed to form a sidewall for engagement with panel 60 as described above.

In addition, instrument 10 can have alternative or additional features from those described above. For instance, sidewall 44 and panel 60 may be configured to engage each other in alternative ways. For example, in one embodiment, sidewall 44 may slope outwardly from boundary surface 48 to backing surface 42 such that sidewall 44 intersects backing surface 42 at an acute angle forming a wedge-shaped channel (not shown) about the perimeter of backing surface 42. In such embodiment, panel 60 may not include tabs 66*a-h* and may be positioned over backing surface 42 such that edges 64 of panel 60 are positioned within the channel and retained therein. In another embodiment, such wedge-shaped channel may only be formed along two opposing sides of sidewall 44, while the remaining sides may or may not include slots 46*a-h* for tabs 66*a-h*.

Other alternative/additional features can include curved backing and/or boundary surfaces 42, 48. For example, boundary surface 48 may be curved in two-planes, particularly in planes defined by the width (W) and depth (D) (best shown in FIG. 3) and height (H) and depth (D) (best shown in FIG. 6) of door 30. However, in one embodiment, boundary surface 48 may be curved in only one of the above mentioned planes and linear in the other. Alternatively, boundary surface 48 may be linear in both the W-D and H-D planes.

Similarly, backing surface 42 can be linear or curved in any one of the planes defined above. In addition, where backing surface 42 is curved, such curvature may be complementary to the curvature of boundary surface 48 in the same plane. However, where boundary surface 48 is curved, backing surface 42 need not be curved, and vice versa. A curved backing surface 42 can help retain a decorative feature between panel 60 and backing surface 42. In addition, backing surface 42 may include resilient members, such as springs and elastomeric pads, installed thereon. Such resilient members may also help secure a decorative feature.

Figure 7A:
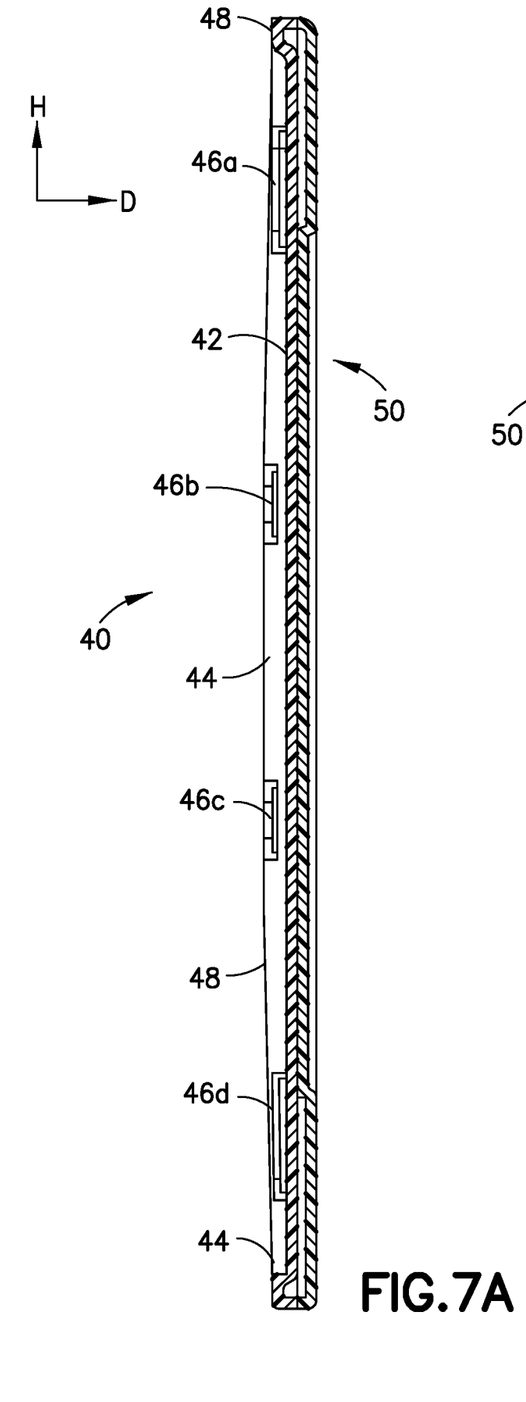
FIG. 7A is a cross-sectional view taken along line A-A of FIG. 5.
Figure 7B:
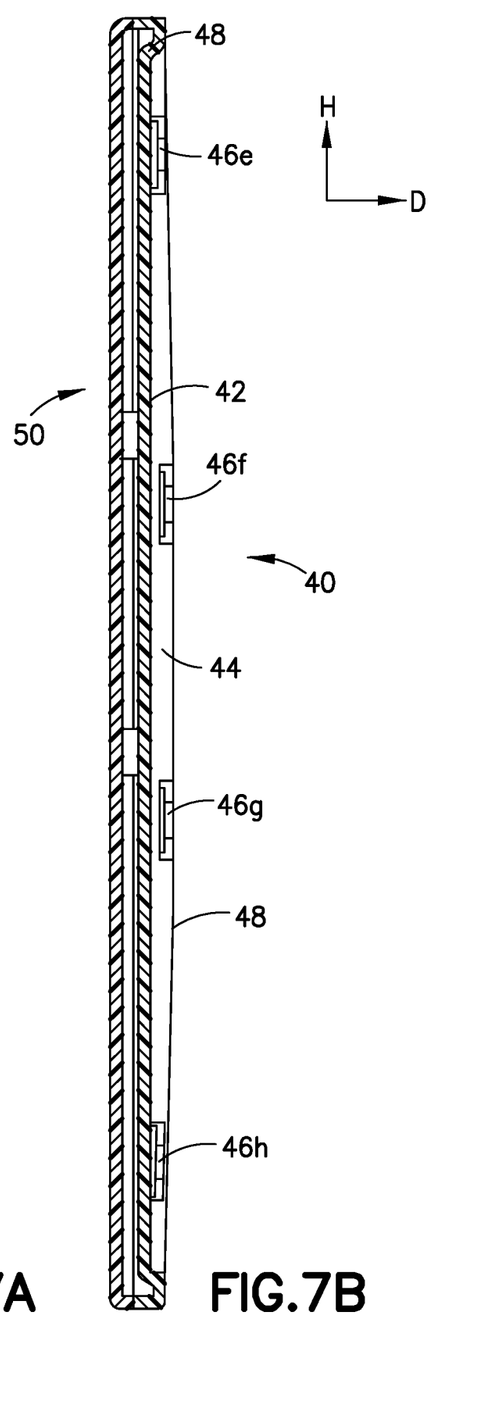
FIG. 7B is a cross-sectional view taken along line B-B of FIG. 5.

Sidewall 44 is generally planar and disposed intermediate boundary surface 48 and backing surface 42. FIGS. 7A and 7B, which are cross-sections taken at lines A-A and B-B of FIG. 5, respectively, exemplifies an influence of the relative curvatures, or lack thereof, of backing surface 42 and boundary surface 48 on the geometry of sidewall 44. In the embodiment of front side 40 depicted, backing surface 42 is planar and boundary surface 48 is curved in the H-D plane. In such embodiment, sidewall 44 takes on a bow-like shape in the H-D plane, where the depth of sidewall 44 is greatest near a center of one side of sidewall 44 and smallest near an intersecting side of sidewall 44.

In addition, slots 46*a-h* may be positioned or arranged along a curved path defined by boundary surface 48, which is also illustrated by FIGS. 7A and 7B. This provides a slight curvature to panel 60 when engaged to sidewall 44, which can deflect glare and/or provide depth to a decorative feature placed behind panel 60. Such curvature of panel 60 may be a compound curvature where panel 60 is curved in both the H-D and W-D planes, or a single curvature where panel 60 is curved in the H-D plane and linear in the W-D plane. In addition, the curvature imposed on panel 60 by slot/tab engagement may be predetermined to match the curvature of the boundary surface 48 in the same plane. Matching curvatures can enhance the decorative appeal of instrument 10.

In one embodiment, such curvature can also be achieved by dimensioning panel 60 to be slightly larger than sidewall 44 such that panel 60 is slightly compressed by sidewall 44 when engaged thereto. This may also provide curvature to panel 60 and facilitate sealing of the space between the backing surface and panel 60. In another embodiment, panel 60 can be molded or thermally treated to form the desired compound or single curvature.

In any embodiment where a curvature is provided to panel 60, the width and height of tabs 46*a-h* may be selected to allow for a smooth curvature as tabs that are too wide and tall may add rigidity to the panel that can harm the smoothness of the curve. For example, tabs 46*a-h* may have a width of 5 mm or less or 2 mm or less.

Figure 9A:
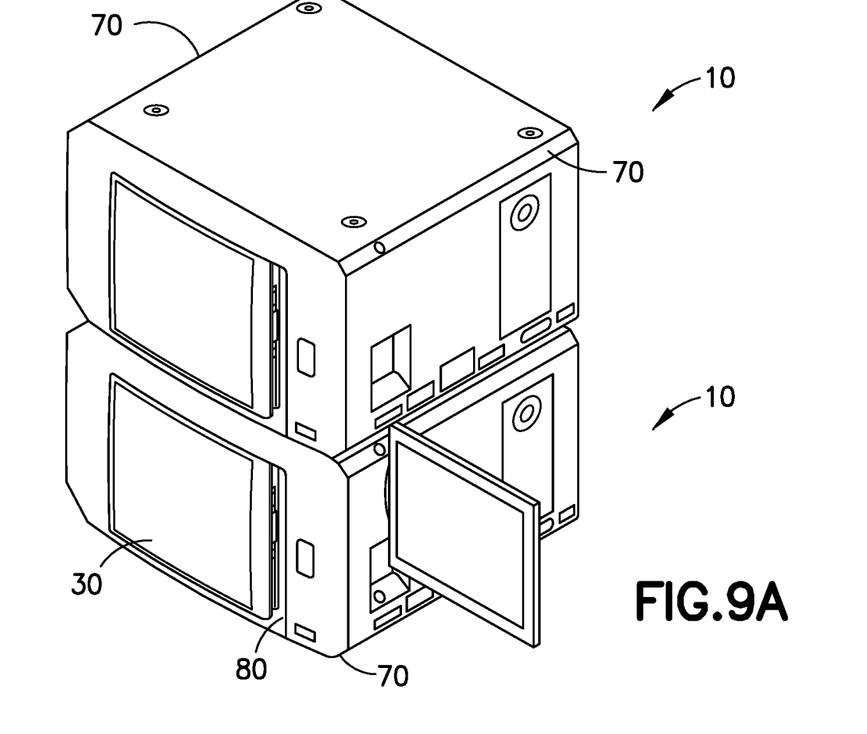
FIG. 9A is a front perspective view of a stacked arrangement of exemplary laboratory instruments.
Figure 9B:
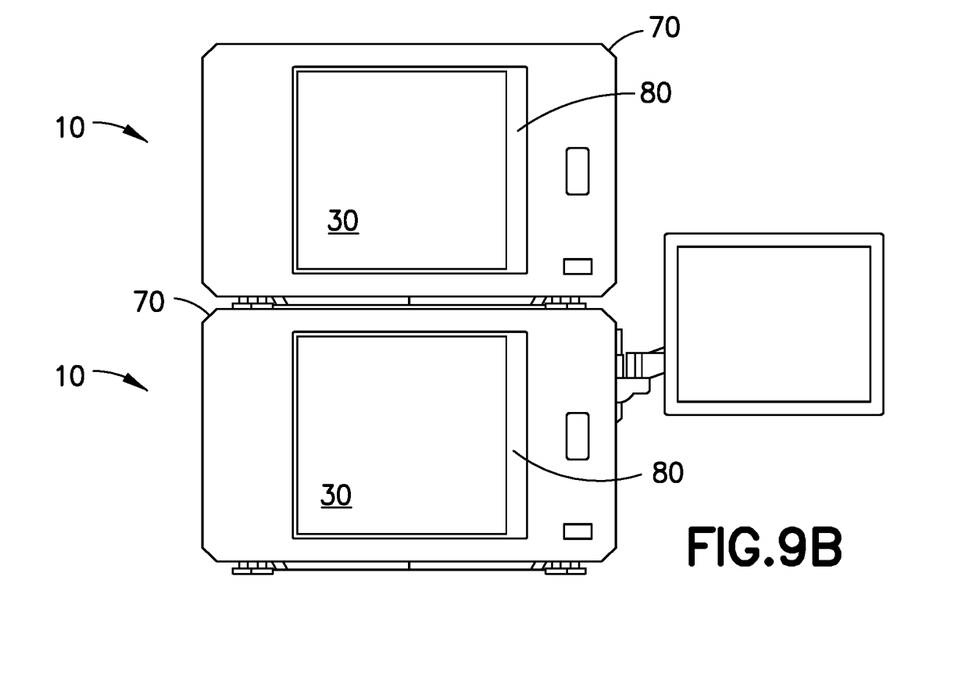
FIG. 9B is a front view of the stacked arrangement of FIG. 9A.
Figure 9C:
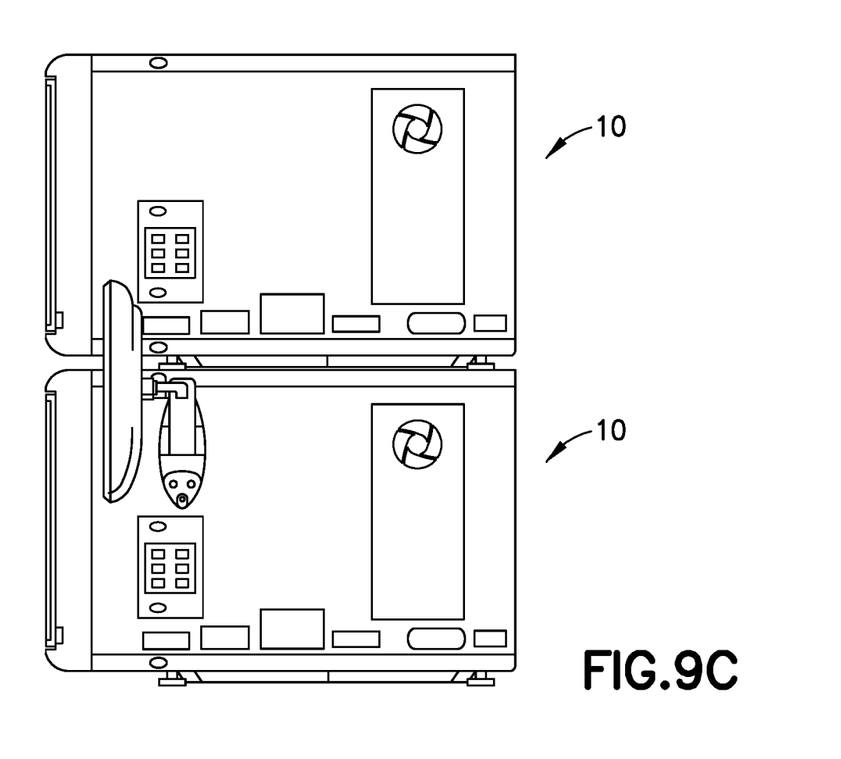
FIG. 9C is a side view of the stacked arrangement FIG. 9A.
Figure 9D:
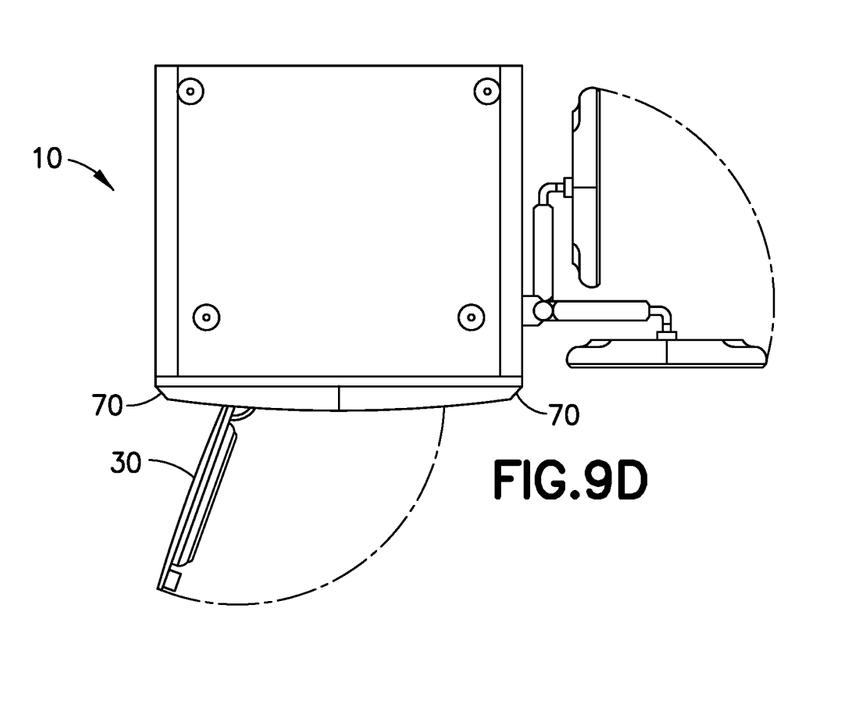
FIG. 9D is a top view of the stacked arrangement of FIG. 9A.

FIGS. 9A-9D illustrate a stacked arrangement of customizable laboratory instruments 10. In this arrangement, the decorative feature for each instrument in the stack can be different or the same. In addition, the decorative features in the stack can be selected to complement each other in color and/or style adding further flare to the laboratory environment. As can be seen in FIG. 9B, the instruments 10 have chamfered edges 70. The chamfered edges 70 provide a softer look that complements the corners of door 30, and the housing inset 80 in which door 30 is positioned.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A customizable laboratory instrument comprising:
a housing defining an interior space for receipt of test materials therein, the housing comprising at least one exterior surface that has an indented backing surface with a raised boundary surface at at least a portion of its perimeter, and a sidewall, the backing surface being offset from the boundary surface a distance substantially equal to a depth of the sidewall; and
a panel having an edge adapted to be received by the sidewall such that a space is defined between the panel and backing surface wherein the space receives a decorative object therein that has a perimeter within the perimeter of the sidewall and wherein the sidewall slopes outwardly from the boundary surface to the backing surface forming a channel therebetween for receipt of the panel.

2. The instrument of claim 1, wherein the exterior surface is located on a door of the instrument.

3. The instrument of claim 1, wherein the exterior surface is located on an exposed surface of the instrument.

4. The instrument of claim 1, wherein the instrument is an 1D/AST instrument.

5. The instrument of claim 1, wherein the panel includes a plurality tabs extending from an edge thereof and the sidewall includes a plurality of slots extending therein, wherein each slot is adapted to receive a respective panel tab.

6. The instrument of claim 5, wherein the tabs on one side of the panel are longer than the tabs on the opposite side of the panel.

7. The instrument of claim 5, wherein at least one of the tabs extends from the edge a longer distance than the remainder of the tabs.

8. The instrument of claim 5, wherein the slots are arranged to cause the panel to curve when the panel tabs are disposed in the slots.

9. The instrument of claim 5, wherein the sidewall defines a quadrilateral and at least and the sidewall that defines the quadrilateral includes at least one slot.

10. The instrument of claim 9, wherein the panel is a quadrilateral complementary to that defined by the sidewalls, and at least two or more sides of the panel edge each include at least one tab to be received by a corresponding slot in the sidewall.

11. The instrument of claim 10, wherein a first panel edge has at least four tabs, and a second panel edge includes at least four tabs.

12. The instrument of claim 11, wherein a first and second tab of the first panel edge extend along the first panel edge a longer distance than a third and fourth tab of the first panel edge.

13. The instrument of claim 1 wherein the panel is approximately rectangular with a height dimension and a width dimension and the panel has an approximately convex surface in at least one dimension.

14. The instrument of claim 13 wherein the panel has an approximately convex surface in both height and width dimensions.

15. A customizable laboratory instrument comprising:
a housing defining an interior space for receipt of test materials therein,
a door for access to the interior space, the door having an exterior surface comprising a raised boundary surface surrounding a recessed backing surface, and a sidewall, the recessed backing surface being offset from the boundary surface a distance substantially equal to a depth of the sidewall; and
a panel having at least one edge adapted to be received by the sidewall wherein an object can be removably placed in the offset space between the panel and backing surface wherein the object has a perimeter within a perimeter of the sidewall and wherein the sidewall slopes outwardly from the boundary surface to the backing surface forming a channel therebetween for receipt of the panel.

16. The instrument of claim 15, wherein the instrument is an ID/AST instrument.

17. The instrument of claim 15, wherein the panel includes a plurality tabs extending from an edge thereof and the sidewall includes a plurality of slots extending therein for receipt of the tabs.

18. The instrument of claim 15, wherein the sidewall defines a quadrilateral such that two opposite sidewalls each include a plurality of slots.

19. The instrument of claim 17, wherein the tabs on one edge of the panel extend further from that edge than the tabs on the opposite edge of the panel.

20. The instrument of claim 15 wherein the panel is approximately rectangular with a height dimension and a width dimension and the panel has an approximately convex surface in at least one dimension.

21. The instrument of claim 20 wherein the panel has an approximately convex surface in both height and width dimensions.

* * * * *

UNITED STATES PATENT AND TRADEMARK OFFICE
CERTIFICATE OF CORRECTION

Page 1 of 1

PATENT NO. : 10,836,988 B2
APPLICATION NO. : 15/574196
DATED : November 17, 2020
INVENTOR(S) : Scott Shindledecker et al.

It is certified that error appears in the above-identified patent and that said Letters Patent is hereby corrected as shown below:

In the Claims

Column 7, Line 53, Claim 9 should read:
- "a quadrilateral and the sidewall that defines the" -.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*